United States Patent [19]

Brenner et al.

[11] 3,933,811
[45] Jan. 20, 1976

[54] N-AMINOMETHYL-2-AMINO(AND 2-AMINO-METHYL)-2-(2-QUINOLYL)-THIOACETAMIDES

[75] Inventors: L. Martin Brenner, Upper Darby; Bernard Loev, Broomall, both of Pa.

[73] Assignee: SmithKline Corporation, Philadelphia, Pa.

[22] Filed: Sept. 18, 1974

[21] Appl. No.: 507,107

Related U.S. Application Data

[62] Division of Ser. No. 266,024, June 26, 1972, Pat. No. 3,853,865.

[52] U.S. Cl.... 260/246 B; 260/247.1 M; 260/283 S
[51] Int. Cl.² ............... C07D 295/10; C07D 295/12
[58] Field of Search ...... 260/283 S, 246 B, 247.1 M

[56] References Cited
UNITED STATES PATENTS

| | | | |
|---|---|---|---|
| 3,660,592 | 1/1975 | Loev | 260/283 S |
| 3,726,878 | 4/1973 | Kanai et al. | 260/283 S |
| 3,740,409 | 6/1973 | Brenner et al. | 260/283 S |
| 3,749,728 | 7/1973 | Loev | 260/283 S |
| 3,825,547 | 7/1974 | Loev | 260/283 S |
| 3,876,645 | 4/1975 | Kanai | 260/283 S |
| 3,880,860 | 4/1975 | Loev | 260/283 S |
| 3,882,126 | 5/1975 | Brenner et al. | 260/283 S |

*Primary Examiner*—Nicholas S. Rizzo
*Assistant Examiner*—Mary C. Vaughn
*Attorney, Agent, or Firm*—Joan S. Keps; Richard D. Foggio; William H. Edgerton

[57] ABSTRACT

The compounds are N-aminomethyl-2-amino(and 2-aminomethyl)-2-heterocyclic-thioacetamides which are inhibitors of gastric acid secretion.

4 Claims, No Drawings

N-AMINOMETHYL-2-AMINO(AND 2-AMINO-METHYL)-2-(2-QUINOLYL)-THIOACETAMIDES

This is a division of application Ser. No. 266,024 filed June 26, 1972, now U.S. Pat. No. 3,853,865.

This invention relates to new N-aminomethyl-2-amino- (and 2-aminomethyl)-2-heterocyclic-thioacetamides having pharmacological activity. In particular, these compounds inhibit gastric acid secretion.

The compounds of this invention are represented by the following formula:

FORMULA I

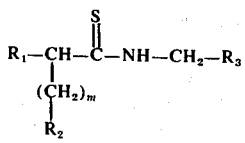

in which:

$m$ is 0 or 1;

$R_1$ is 2-pyridyl, 2-pyrimidyl, 4-pyrimidyl, 2-pyrazinyl, 2-pyrrolyl, 2-quinolyl, 2-thiazolyl or 4-thiazolyl; and $R_2$ and $R_3$ are di-lower alkylamino, N-lower alkyl-N-phenylamino, piperidino, pyrrolidino, morpholino or N-lower alkylpiperazino.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the heterocyclic rings of $R_1$ and the phenyl rings. These compounds are used as are the parent compounds.

Preferred compounds of this invention are represented by Formula I in which $m$ is 0 or 1 and $R_2$ is dimethylamino, diethylamino, piperidino or pyrrolidino or $m$ is 1 and $R_2$ is morpholino, and $R_3$ is di-lower alkylamino, piperidino, pyrrolidino or morpholino.

Most preferably, in the compounds of Formula I, $R_1$ is pyridyl.

Advantageous compounds of this invention are represented by Formula I in which $R_1$ is 2-pyridyl, $m$ is 0 or 1 and $R_2$ is dimethylamino or $m$ is 1 and $R_2$ is morpholino, and $R_3$ is diethylamino, pyrrolidino or morpholino.

A particularly advantageous compound of this invention is 3-morpholino-N-morpholinomethyl-2-(2-pyridyl)-thiopropanamide.

The compounds of this invention produce inhibition of gastric acid secretion. This activity is demonstrated by administration to pylorus ligated rats at doses of about 10 to about 50 mg./kg. orally. Also, this activity is demonstrated by administration to chronic gastric fistula rats (Brodie et al., Amer. J. Physiol. 202:812–814, 1962) at doses of about 30 to about 50 mg./kg. orally. In these procedures, compounds which produce an increase in the gastric pH or a decrease in the volume of gastric juice or both are considered active.

These compounds shown antiulcer activity in the restraint-stress method in which on oral administration to rats these compounds inhibit the development of experimental ulcers.

The compounds of this invention are prepared as follows:

I.

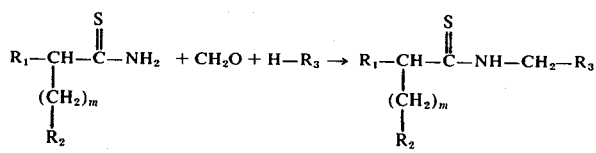

The terms $m$, $R_1$, $R_2$ and $R_3$ are as defined above.

II.

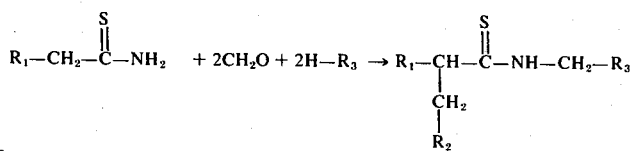

The terms $m$, $R_1$, $R_2$ and $R_3$ are as defined above and $R_2$ and $R_3$ are the same.

According to procedure I, a 2-amino(or 2-aminomethyl)-2-heterocyclic-thioacetamide is reacted with formaldehyde and an amine. The reaction is preferably carried out in an organic solvent, such as a lower alkanol, for example methanol. The reaction is carried out at about −40°C. to about 90°C.

According to procedure II, a heterocyclic thioacetamide is reacted with two molar equivalents of formaldehyde and two molar equivalents of an amine to give compounds of this invention in which $m$ is 1 and $R_2$ and $R_3$ are the same.

The 2-amino(or 2-aminomethyl)-2-heterocyclicthioacetamide starting materials are prepared by the following procedures.

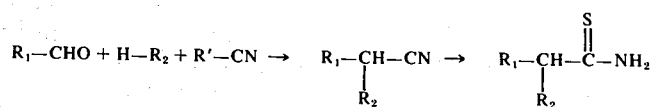

The terms $R_1$ and $R_2$ are as defined above and $R'$ is an alkali metal.

According to the above procedure, a heterocyclic-carboxaldehyde, and amine and an alkali metal cyanide are reacted, preferably in the presence of acid, to give a 2-amino-2-heterocyclic-acetonitrile which is converted to a 2-amino-2-heterocyclic-thioacetamide by reacting with hydrogen sulfide in the presence of a base such as an amine or by reacting with ammonium polysulfide.

The 2-aminomethyl-2-heterocyclic-thioacetamide starting materials are prepared by reacting a 2-heterocyclicthioacetamide, 2-heterocyclic-acetamide, or 2-heterocyclicacetonitrile with an equimolar amount of formaldehyde and an equimolar amount of an amine to give the corresponding 2-aminomethyl compounds and where the intermediate is a 2-aminomethyl-2-heterocyclic-acetamide, reacting with phosphorus pentasulfide to give the corresponding thioacetamide and where the intermediate is 2-aminomethyl-2-heterocyclicacetonitrile, reacting with hydrogen sulfide in the presence of a base such as an amine or by reacting with ammonium polysulfide to give the corresponding thioacetamide.

The pharmaceutically acceptable acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, succinate, oxalate, benzoate, methanesulfonate, ethanedisulfonate, benzenesulfonate, acetate, propionate, tartrate, citrate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, galatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The terms "lower alkyl" and "lower alkoxy" where used herein denote groups having 1-4 carbon atoms and "halogen" denotes chloro, bromo or fluoro.

The following examples are not limiting but are illustrative of the compounds of this invention and processes for their preparation.

EXAMPLE 1

2-(2-Pyridyl)thioacetamide (0.7 g., 0.0046 mole) is dissolved in 10 ml of methanol. The solution is cooled to about −40°C. and 1.0 g (0.012 mole) of morpholine and 0.9 g. (0.012 mole) of 37% aqueous formaldehyde solution are added simultaneously. The mixture is allowed to stand at −20°C. for 48 hours, then the solvent is removed under reduced pressure (no heat is applied). The viscous liquid is chromatographed on an acetone slurried Florisil (magnesiasilica gel) column. The yellow eluant is collected, the solvent removed and the residual liquid applied to an ethyl acetate slurried Florisil (magnesia-silica gel) column. Again the yellow eluant is concentrated and the residual viscous liquid is triturated with ethyl acetate and left at −20°C. for 18 hours. The resulting precipitate is filtered and washed with cold ethyl acetate to give 3-morpholino-N-morpholinomethyl-2-(2-pyridyl)thiopropanamide, m.p. 109°–111°C.

EXAMPLE 2

To cold 2-pyridinecarboxaldehyde (21.4 g., 0.2 mole) is added dimethylamine (22.5 g. of a 40% aqueous solution, 0.2 mole) and the solution is neutralized with concentrated hydrochloric acid. To the stirred neutralized solution is added 14.4 g. (0.22 mole) of potassium cyanide. The mixture is stirred overnight, then diluted with water, transferred to a separatory funnel and repeatedly extracted with chloroform. The combined chloroform extracts are washed three times with water, once with brine and dried over magnesium sulfate. The mixture is filtered, the solvent is removed under reduced pressure and methanol is added to the residue. The mixture is allowed to stand at −20°C. for 18 hours, then filtered. The filtrate is concentrated and distilled in vacuo to give 2-dimethylamino-2-(2-pyridyl)acetonitrile.

2-Dimethylamino-2-(2-pyridyl)acetonitrile (11.4 g., 0.07 mole) is dissolved in 200 ml. of dry pyridine containing 5 ml of anhydrous triethylamine. Hydrogen sulfide is bubbled into the stirred solution for 7 hours and the solution is then stirred for 17 hours. This procedure is repeated for 5 days. Then the mixture is stirred for an additional 48 hours. The solvent is then removed under reduced pressure and the residue is recrystallized from ethanol to give 2-dimethylamino-2-(2-pyridyl)thioacetamide, m.p. 130°–133°C. (dec.).

To a solution of 1.8 g. (0.0091 mole) of 2-dimethylamino-2-(2-pyridyl)thioacetamide in 25 ml. of methanol is added 0.9 g. (0.0015 mole) of morpholine in 2 ml. of methanol and 0.9 g. (0.0015 mole) of 37% aqueous formaldehyde solution in 2 ml. of methanol. The resulting solution is stirred at room temperature for 18 hours. The solvent is removed under reduced pressure and ether is added to the residue. The mixture is cooled at −20°C. for 4 hours and then filtered. The solvent is evaporated from the filtrate to give 2-dimethylamino-N-morpholinomethyl-2-(2-pyridyl)-thioacetamide.

EXAMPLE 3

Hydrogen sulfide is bubbled into a stirred solution of 10.0 g. (0.048 mole) of 2-morpholino-2-(2-pyridyl)-acetonitrile, dissolved in 200 ml. of dry pyridine containing 5 ml. of anhydrous triethylamine, for 7 hours and then the mixture is stirred for 17 hours. Hydrogen sulfide is again bubbled into the stirred mixture and the mixture is again stirred for 17 hours. Then the solvent is removed under reduced pressure and the residue is recrystallized from ethanol to give 2-morpholino-2-(2-pyridyl)thioacetamide, m.p. 172°–175°C. (dec.).

2-Morpholino-2-(2-pyridyl)thioacetamide (1.0 g., 0.0042 mole) is dissolved with heating in 30 ml. of methanol. To the warm solution is added 1.0 g. (0.012 mole) of morpholine and 1.84 g. (0.022 mole) of 37% aqueous formaldehyde solution. The resulting solution is refluxed three hours and then stirred for 17 hours. The solvent is evaporated and the residue is recrystallized from methanol/ether to give 2-morpholino-N-morpholinomethyl-2-(2-pyridyl)thioacetamide, m.p. 144°–147°C. (dec.).

EXAMPLE 4

By the procedure of Example 1, using in place of morpholine, the following amines:
  pyrrolidine
  piperidine
  1-methylpiperazine
  diethylamine
the products are, respectively:
  3-pyrrolidino-N-pyrrolidinomethyl-2-(2-pyridyl)-thiopropanamide
  3-piperidino-N-piperidinomethyl-2-(2-pyridyl)-thiopropanamide
  3-(4-methylpiperazino)-N-(4-methylpiperazinomethyl)-2-(2-pyridyl)thiopropanamide
  3-diethylamino-N-diethylaminomethyl-2-(2-pyridyl)-thiopropanamide.

EXAMPLE 5

By the procedure of Example 1, using in place of 2-(2-pyridyl)thioacetamide, the following thioacetamides:
  2-(2-pyrazinyl)thioacetamide
  2-(2-pyrrolyl)thioacetamide
  2-(2-quinolyl)thioacetamide
  2-(6-methyl-2-pyridyl)thioacetamide
  2-(4-methoxy-2-pyridyl)thioacetamide
  2-(4,6-dimethyl-2-pyrimidyl)thioacetamide
the products are, respectively:
  3-morpholino-N-morpholinomethyl-2-(2-pyrazinyl)-thiopropanamide
  3-morpholino-N-morpholinomethyl-2-(2-quinolyl)-thiopyropanamide
  3-morpholino-N-morpholinomethyl-2-(2-quinolyl)-thiopropanamide
  3-morpholino-N-morpholinomethyl-2-(6-methyl-2-pyridyl)thiopropanamide
  3-morpholino-N-morpholinomethyl-2-(4-methoxy-2-pyridyl)thiopropanamide
  3-morpholino-N-morpholinomethyl-2-(4,6-dimethyl-2pyrimidyl)thiopropanamide.

EXAMPLE 6

By the procedure of Example 2, using in place of 2-dimethylamino-2-(2-pyridyl)acetonitrile, the following acetonitriles:
  2-diethylamino-2-(2-pyridyl)acetonitrile
  2-pyrrolidino-2-(2-pyridyl)acetonitrile
  2-piperidino-2-(2-pyridyl)acetonitrile
  2-dimethylamino-2-(2-quinolyl)acetonitrile
  2-piperidino-2-(2-quinolyl)acetonitrile
the products are, respectively:
  2-diethylamino-N-morpholinomethyl-2-(2-pyridyl)-thioacetamide
  N-morpholinomethyl-2-pyrrolidino-2-(2-pyridyl)thioacetamide
  N-morpholinomethyl-2-piperidino-2-(2-pyridyl)thioacetamide
  2-dimethylamino-N-morpholinomethyl-2-(2-quinolyl)thioacetamide
  N-morpholinomethyl-2-piperidino-2-(2-quinolyl)thioacetamide.

EXAMPLE 7

To 27.0 g. of 2-pyrimidinecarboxaldehyde and 11.3 g. of dimethylamine (neutralized with hydrochloric acid) is added, with stirring and cooling, 17.9 g. of potassium cyanide in a small amount of water. The mixture is allowed to stand overnight and ether is added. Concentrating and distilling the residue gives 2-dimethylamino-2-(2-pyrimidyl)acetonitrile.

Using 2-dimethylamino-2-(2-pyrimidyl)acetonitrile in place of 2-dimethylamino-2-(2-pyridyl)acetonitrile in the procedure of Example 2 gives 2-dimethylamino-N-morpholinomethyl-2-(2-pyrimidyl)thioacetamide.

EXAMPLE 8

By the procedure of Example 2, using the following carboxaldehydes in place of 2-pyridinecarboxaldehyde:
  4-pyrimidinecarboxaldehyde
  2-pyrazinecarboxaldehyde
  2-pyrrolecarboxaldehyde
  2-thiazolecarboxaldehyde
  4-thiazolecarboxaldehyde
the products are, respectively:
  2-dimethylamino-N-morpholinomethyl-2-(4-pyrimidyl)thioacetamide
  2-dimethylamino-N-morpholinomethyl-2-(2-pyrazinyl)thioacetamide
  2-dimethylamino-N-morpholinomethyl-2-(2-pyrrolyl)thioacetamide
  2-dimethylamino-N-morpholinomethyl-2-(2-thiazolyl)thioacetamide
  2-dimethylamino-N-morpholinomethyl-2-(4-thiazolyl)thioacetamide.

EXAMPLE 9

By the procedure of Example 2, using diethylamine in place of dimethylamine, the product is 2-diethylamino-N-morpholinomethyl-2-(2-pyridyl)thioacetamide.

Similarly, using dipropylamine, the product is 2-dipropylamino-N-morpholinomethyl-2-(2-pyridyl)thioacetamide.

By the same procedure, using dibutylamine, the product is 2-dibutylamino-N-morpholinomethyl-2-(2-pyridyl)thioacetamide.

EXAMPLE 10

By the procedure of Example 1, using in place of morpholine the following 1-lower alkylpiperazines:
  1-ethylpiperazine
  1-propylpiperazine
  1-butylpiperazine
the products are, respectively:
  3-(4-ethylpiperazino-N-(4-ethylpiperazinomethyl)-2-(2-pyridyl)thiopropanamide
  3-(4-propylpiperazino)-N-(4-propylpiperazinomethyl)-2-(2-pyridyl)thiopropanamide 3-(4-butylpiperazino)-N-(4-butylpiperazinomethyl)-2-(2-pyridyl)thiopropanamide.

EXAMPLE 11

By the procedure of Example 2, using the following 1-lower alkylpiperazines in place of dimethylamine:
1-methylpiperazine
1-ethylpiperazine
1-propylpiperazine
1-butylpiperazine
the products are, respectively:
2-(4-methylpiperazino)-N-morpholinomethyl-2-(2-pyridyl)thioacetamide
2-(4-ethylpiperazino)-N-morpholinomethyl-2-(2-pyridyl)thioacetamide
N-morpholinomethyl-2-(4-propylpiperazino)-2-(2-pyridyl)thioacetamide
2-(4-butylpiperazino)-N-morpholinomethyl-2-(2-pyridyl)thioacetamide.

EXAMPLE 12

A solution of 3.0 g. (0.019 mole) of 2-(2-pyridyl)thioacetamide in 40 ml. of anhydrous methanol is treated at −40°C. with 1.7 g. (0.019 mole) of morpholine in 5 ml. of methanol and 1.6 ml. of 37% formalin solution. The resulting mixture is kept at −25°C. for 36 hours.

The solvents are evaporated in vacuo at 25°C. and the residue is triturated three times with ether in the cold. The ether is decanted and the residue is recrystallized from acetone/hexane to give 3-morpholino-2-(2-pyridyl)thiopropanamide.

The above prepared 3-morpholino-2-(2-pyridyl)thiopropanamide is reacted with pyrrolidine and formaldehyde in methanol by the procedure of Example 2 to give 3-morpholino-N-pyrrolidinomethyl-2-(2-pyridyl)-thiopropanamide.

By the same procedure, using the following compounds in place of pyrrolidine:
dimethylamine
diethylamine
piperidine
1-methylpiperazine
the products are, respectively:
N-dimethylaminomethyl-3-morpholino-2-(2-pyridyl)thiopropanamide
N-diethylaminomethyl-3-morpholino-2-(2-pyridyl)-thiopropanamide
3-morpholino-N-piperidinomethyl-2-(2-pyridyl)thiopropanamide
N-(4-methylpiperazinomethyl)-3-morpholino-2-(2-pyridyl)thiopropanamide.

EXAMPLE 13

One gram of 3-morpholino-N-morpholinomethyl-2-(2-pyridyl)thiopropanamide in ethanol is treated with ethereal hydrogen chloride and the solvents are removed under reduced pressure to give 3-morpholino-N-morpholinomethyl-2-(2-pyridyl)thiopropanamide trihydrochloride.

Similarly, using ethereal hydrogen bromide, the hydrobromide salt is prepared.

EXAMPLE 14

2-Dimethylamino-N-morpholinomethyl-2-(2-pyridyl)thioacetamide in ethanol is treated with an equimolar amount of oxalic acid in ethanol to give, after removing the solvent under reduced pressure, 2-dimethylamino-N-morpholinomethyl-2-(2-pyridyl)-thioacetamide oxalate.

Similarly, using maleic acid, 2-dimethylamino-N-morpholinomethyl-2-(2-pyridyl)thioacetamide maleate is prepared.

In the same manner, using citric acid, 2-dimethylamino-N-morpholinomethyl-2-(2-pyridyl)thioacetamide citrate is prepared.

EXAMPLE 15

Using N-methylaniline in place of morpholine in the procedure of Example 1, the product is 3-(N-methyl-N-phenylamino)-N-(N-methyl-N-phenylaminomethyl)-2-(2-pyridyl)thiopropanamide.

Similarly, using N-ethylaniline, the product is 3-(N-ethyl-N-phenylamino)-N-(N-ethyl-N-phenylaminomethyl)-2-(2-pyridyl)thiopropanamide.

By the same procedure, using the appropriate N-lower alkylanilines, the products are 3-(N-propyl-N-phenylamino)-N-(N-propyl-N-phenylaminomethyl)-2-(2-pyridyl)thiopropanamide and 3-(N-butyl-N-phenylamino)-N-(N-butyl-N-phenylaminomethyl)-2-(2-pyridyl)thiopropanamide.

EXAMPLE 16

Using N-methylaniline in place of dimethylamine in the procedure of Example 2, the product is 2-(N-methyl-N-phenylamino)-N-morpholinomethyl-2-(2-pyridyl)thioacetamide.

Similarly, using the appropriate N-lower alkylanilines, the corresponding N-ethyl, N-propyl and N-butyl compounds are prepared.

EXAMPLE 17

By the procedure of Example 2, using in place of morpholine, the following amines:
pyrrolidine
piperidine
1-methylpiperazine
diethylamine
the products are, respectively:
2-dimethylamino-N-pyrrolidinomethyl-2-(2-pyridyl)thioacetamide
2-dimethylamino-N-piperidinomethyl-2-(2-pyridyl)-thioacetamide
2-dimethylamino-N-(4-methylpiperazinomethyl)-2-(2-pyridyl)thioacetamide
2-dimethylamino-N-diethylaminomethyl-2-(2-pyridyl)thioacetamide.

What is claimed is:
1. A compound of the formula:

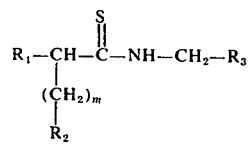

in which
 m is 0 or 1;
 $R_1$ is 2-quinolyl; and
 $R_2$ and $R_3$ are di-lower alkylamino, N-lower Alkyl-N-phenylamino, piperidino, pyrrolidino or morpholino
or a pharmaceutically acceptable acid addition salt thereof.

2. A compounds of claim 1 in which $m$ is 0 or 1 and $R_2$ is dimethylamino, diethylamino, piperidino or pyrrolidino or m is 1 and $R_2$ is morpholino, and $R_3$ is di-lower alkylamino, piperidino, pyrrolidino or morpholino.

3. A compound of claim 1, said compound being 3-morpholino-N-morpholinomethyl-2-(2-quinolyl)thiopropanamide.

4. A compound of claim 1, said compound being 2-dimethylamino-N-morpholinomethyl-2-(2-quinolyl)-thioacetamide.

* * * * *

UNITED STATES PATENT AND TRADEMARK OFFICE
CERTIFICATE OF CORRECTION

PATENT NO. : 3,933,811
DATED : January 20, 1976
INVENTOR(S) : L. Martin Brenner and Bernard Loev It is certified that error appears in the above-identified patent and that said Letters Patent are hereby corrected as shown below:

Column 3, line 2, "and amine" should read -- an amine -- .

Column 5, lines 49-50, "(2-quinolyl)-thiopyropanamide" should read -- (2-pyrrolyl)-thiopropanamide -- .

Column 8, line 64, "Alkyl-N-" should read -- alkyl-N- -- .

Signed and Sealed this twentieth Day of April 1976

[SEAL]

Attest:

RUTH C. MASON
Attesting Officer

C. MARSHALL DANN
Commissioner of Patents and Trademarks